United States Patent [19]

Burks

[11] Patent Number: Plant 6,509

[45] Date of Patent: Jan. 3, 1989

[54] ROSE PLANT NAMED BURYELLOW

[76] Inventor: Joe Burks, P.O. Box 4400, Tyler, Tex. 75712

[21] Appl. No.: 50,145

[22] Filed: May 15, 1987

[51] Int. Cl.[4] ..... A01H 5/00

[52] U.S. Cl. ..... Plt./3

[58] Field of Search ..... Plt./3

*Primary Examiner*—Robert E. Bagwill
*Attorney, Agent, or Firm*—Vincent G. Gioia

[57] ABSTRACT

A new hybrid tea rose variety which is a climbing sport of the rose known as "Sunflare".

1 Drawing Sheet

The present invention relates to a new and distinct variety of rose plant of the hybrid tea rose class, which is a climbing sport (mutation) of the rose known as "Sunflare" which was discovered by me in Tyler, Tex. The denomination of this new rose is "Buryellow".

Among the novel characteristics possessed by this new variety which distinguish it from the cultivar from which it sported and all other varieties of which I am aware are its growth habit as a climber, attaining height of 7 to 7½ feet and its shinier foliage which is darker and denser than the parent cultivar. Asexual reproduction by budding of the new variety as performed in Kern County, Calif., shows that the foregoing and other distinguishing characteristics come true to form and are established and transmitted through succeeding propagations.

The accompanying drawing shows typical specimens of the vegetative growth and flowers of the new variety in different stages of development and as depicted in color as nearly true as it is reasonably possible to make the same in a color illustration of this character.

The following is a detailed description of my new variety, with color terminology in accordance with The Royal Horticultural Society Colour Chart (RHSCC). The terminology used in color description herein refers to plate numbers in the aforementioned color chart, e.g., "18A" is plate 18A of The Royal Horticultural Society Colour Chart.

Parentage: Climbing sport (mutation) of the rose known as "Sunflare".
Class: Climbing Hybrid Tea.

The following observations are made of specimens grown outdoors in Kern County, Calif., during the month of June.

FLOWER

Blooming habit: Continuous.

A. Bud:
- (1) *Size.*—Medium.
- (2) *Form.*—Ovoid.
- (3) *Color.*—As sepals fall, bud color is near Amber yellow 18A to 20A.
- (4) *Sepals.*—Simple with few appendages.
- (5) *Peduncle.*—Length — short. Aspect — strong. Strength — erect. Color — 146C.

B. Bloom:
- (1) *Size.*—Average size when fully expanded — about 3½ inches.
- (2) *Borne.*—Several together in large sprays.

- (3) *Form.*—Ovoid buds open into relatively loose cup-shaped blooms and petals roll under. Blooms open fully upon maturity.
- (4) *Petalage.*—Number of petals under normal conditions — about 20.
- (5) *Color.*—Near Amber yellow ovoid buds open easily initially displaying similar coloring of 18A through 20A before blooms age at which time petals lighten to near white. When fully open, comparatively darker yellow-orange coloring of stamens, pollen and stigma is evident and contrast well with surrounding Amber yellow colored petals. Irregular and random sunbleaching to near white provide additional highlights to the coloring and eventually the near white coloring predominates as flowers age, at which time flower centers darken.

C. Petals:
- (1) *Texture.*—Medium.
- (2) *Appearance.*—Satiny inside and outside.
- (3) *Form.*—Fan shaped.
- (4) *Arrangement.*—Imbricated.
- (5) *Petaloids in center.*—Few.
- (6) *Persistence.*—Tend to persist.
- (7) *Fragrance.*—Slight.
- (8) *Lasting quality.*—Very long lasting on plant and average as cut flower.

REPRODUCTIVE ORGANS

A. Stamens, filaments and anthers:
- (1) *Arrangement.*—Even length arranged around styles.
- (2) *Color.*—Yellow-orange.

B. Pollen:
- *Color.*—Near 15C.

C. Styles: Short, even.

D. Stigmas:
- *Color.*—Reddish-yellow.

E. Hips:
- *Shape.*—Globular, medium.
- *Color.*—Near 33A.
- *Do seeds protrude?*—No.

PLANT

A. Form: Upright, spreading.

B. Growth: Very vigorous, uniform branching, with large basals.
- *Height attained.*—About 7 to 7½ feet.

C. Foliage: Compound 5 leaflets.
- (1) *Size.*—Medium.
- (2) *Quantity.*—Abundant.

(3) *Color.*—New foliage: Upper side — near 144A. Under side — near 144B. Old foliage: Upper side — near 138A. Under side — near 138B.

(4) *Shape.*—Oval, acuminate.

(5) *Texture.*—Upper side is glossy and under side is glaborous.

(6) *Edge.*—Serrated.

(7) *Serration.*—Simple.

(8) *Leaf stem.*—Color — near to 146A. Under side — near 146C.

(9) *Stipules.*—Long.

(10) *Resistance to disease.*—Blackspot — excellent. Mildew — excellent. Rust — above average.

D. Wood:

(1) *New wood.*—Color — near 144B. Bark — smooth.

(2) *Old wood.*—Color — near 146C. Bark — smooth.

E. Thorns:

(1) *Thorns.*—Quantity (main stalk) — ordinary. On laterals from stalk — average. Form — pointed, slight recurve. Length — medium. Color — near 144C. Position — irregular.

(2) *Prickles.*—Few on main stalks, few on laterals.

F. Winter hardiness: Above average winter hardiness.

I claim:

1. A new and distinct variety of rose plant of the hybrid tea class which is a climbing sport of the rose known as "Sunflare", substantially as shown and described, characterized particularly by its climbing habit of growth and shinier foliage which is also darker and denser than "Sunflare".

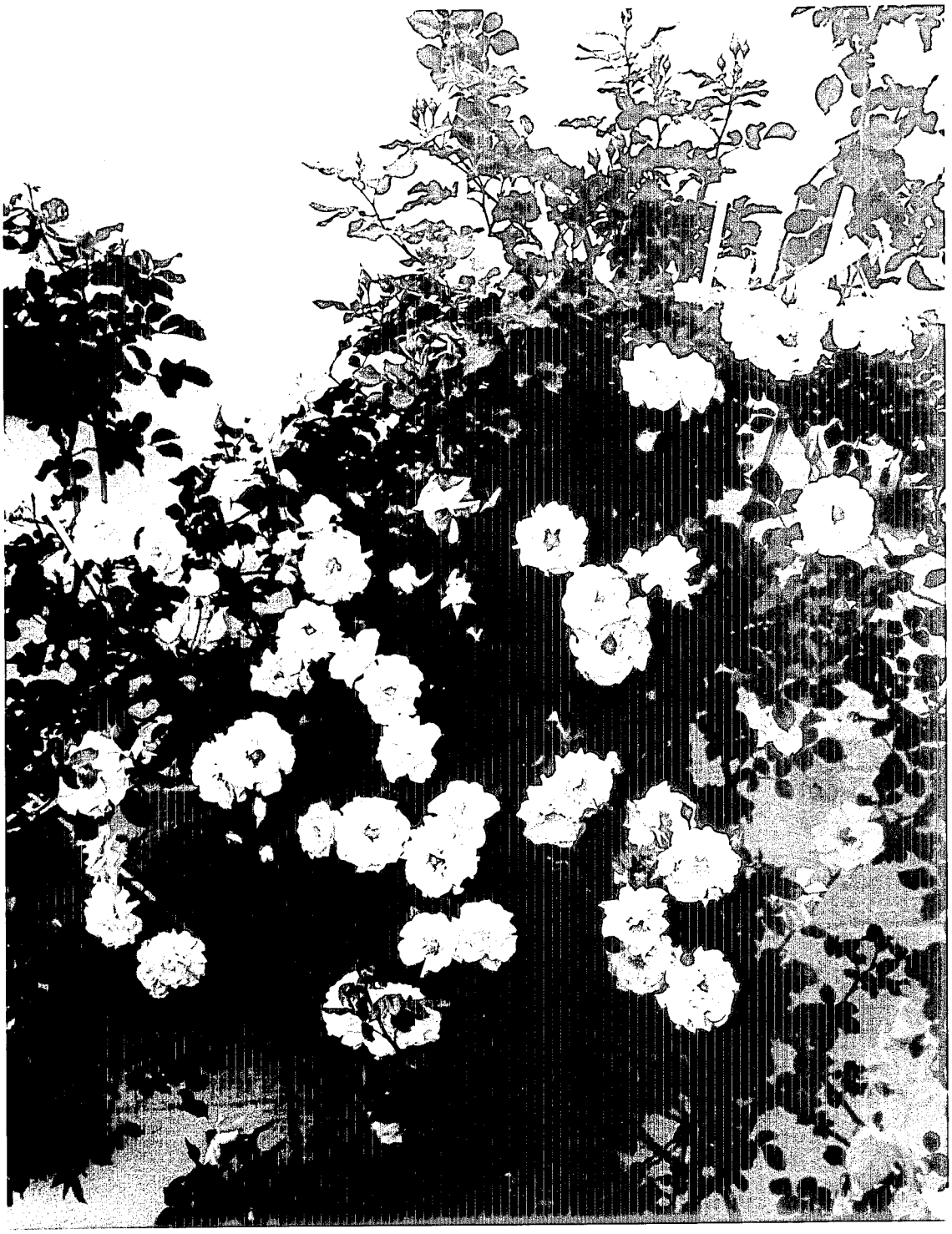

* * * * *